(12) United States Patent
Snyder

(10) Patent No.: US 6,899,733 B2
(45) Date of Patent: *May 31, 2005

(54) INTRAOCULAR LENS WITH IMPROVED HAPTIC AND METHOD OF IMPLANTING SAME

(76) Inventor: Michael E. Snyder, 8561 Chaucer Pl., Cincinnati, OH (US) 45249

( * ) Notice: Subject to any disclaimer, the term of this patent is extended or adjusted under 35 U.S.C. 154(b) by 370 days.

This patent is subject to a terminal disclaimer.

(21) Appl. No.: 10/090,985

(22) Filed: Mar. 4, 2002

(65) Prior Publication Data

US 2002/0091442 A1 Jul. 11, 2002

Related U.S. Application Data

(63) Continuation of application No. 09/520,490, filed on Mar. 8, 2000, now Pat. No. 6,352,542, and a continuation of application No. PCT/US01/05450, filed on Feb. 21, 2001.

(51) Int. Cl.[7] ................................................. A61F 2/16
(52) U.S. Cl. ........................ 623/6.4; 623/6.43; 623/6.47
(58) Field of Search ............................... 606/107, 148; 623/6.11, 6.12, 6.15, 6.18, 6.38, 6.39, 6.4, 6.42, 6.45, 6.46, 6.51, 6.53, 6.54, 6.55

(56) References Cited

U.S. PATENT DOCUMENTS

| | | | |
|---|---|---|---|
| 4,304,012 A | * 12/1981 | Richard | ...................... 623/6.51 |
| 4,349,027 A | 9/1982 | DiFrancesco | |
| D267,041 S | 11/1982 | Hessburg | |
| D267,197 S | 12/1982 | Hessburg | |
| 4,409,690 A | 10/1983 | Gess | |
| 4,434,515 A | 3/1984 | Poler | |
| 4,468,820 A | 9/1984 | Uhler et al. | |
| 4,494,254 A | * 1/1985 | Lopez | ........................ 623/6.42 |
| 4,502,163 A | 3/1985 | Graham | |
| 4,542,541 A | * 9/1985 | Pannu | ........................ 623/6.55 |
| 4,617,023 A | 10/1986 | Peyman | |
| 4,655,223 A | 4/1987 | Kim | |
| 4,836,202 A | * 6/1989 | Krasner | ....................... 606/107 |
| 4,842,600 A | 6/1989 | Feaster | |
| 4,863,465 A | 9/1989 | Kelman | |
| 4,863,539 A | 9/1989 | Lee et al. | |
| 4,961,745 A | 10/1990 | Graham et al. | |
| 5,047,051 A | 9/1991 | Cumming | |
| 5,266,241 A | 11/1993 | Parekh | |
| 5,282,855 A | 2/1994 | Bragg | |
| 5,306,297 A | 4/1994 | Rheinish et al. | |
| 5,336,262 A | 8/1994 | Chu | |
| 5,376,115 A | 12/1994 | Jansen | |
| 5,405,386 A | 4/1995 | Rheinish | |
| 5,507,758 A | 4/1996 | Thomason et al. | |
| 5,746,757 A | 5/1998 | McGuire | |
| D395,512 S | 6/1998 | Korenfeld | |
| 6,152,959 A | 11/2000 | Portney | |
| 6,352,542 B1 | * 3/2002 | Snyder | ........................ 606/148 |

OTHER PUBLICATIONS

Snyder, Michael E., "A Closed–Chamber, Sceleral Tunnel Approach to Sutured PCIOL's," Cinncinnati Eye Institute, (San Diego, CA) Apr., 1998.

* cited by examiner

*Primary Examiner*—Julian W. Woo
(74) *Attorney, Agent, or Firm*—Dobrusin & Thennisch PC

(57) ABSTRACT

Ophthalomogical implant device and procedure employing improved haptic structure, improved suture guide device or both.

14 Claims, 2 Drawing Sheets

INTRAOCULAR LENS WITH IMPROVED HAPTIC AND METHOD OF IMPLANTING SAME

This application is a continuation of application Ser. No. 09/520,490 filed on Mar. 8, 2000 now U.S. Pat. No. 6,352,542 and also claims priority to PCT Application number US01/05450, filed Feb. 21, 2001.

TECHNICAL FIELD

The present invention relates generally to ophthalmologic implants, and more particularly to an intraocular lens having an improved haptic.

BACKGROUND OF THE INVENTION

Modern cataract removal procedures commonly are followed by the implantation of an intraocular lens (IOL) in either the anterior or posterior chamber of the eye. To assist the surgeon typically the implant is made of a foldable, and flexible material. Harder materials have been employed as well. Nonetheless, it is typical that the IOL must be able to be passed through an incision on the order of several millimeters or less, and then be manipulable within the lens capsule for proper positioning.

A typical IOL includes a central lens or optic portion (which replaces the lens of the eye) and a plurality of supporting members, known generally as haptics. Haptics are typically outwardly extending (e.g., radially, tangentially, or the like) structures that are attached to the optic and support the optic within the eye by pressing against adjacent tissue.

In designing IOLs, it is frequently the desire of the designer to provide a haptic structure that permits ready insertion into the lens capsule of the eye and which stabilizes the optic within the eye, helping to prevent undesired lateral, torsional, rotational or twisting and vaulting movement (e.g., with anterior chamber IOLs) within the eye.

The lens capsule of the eye is suspended by fine threadlike zonules. Desirably, implantation of an IOL is accomplished without trauma to the lens capsule or the zonules. For instance, it is common that where inadequate zonular structure is present, an implant than needs to be placed in front of the iris of the eye, or even stitched to the wall of the eye, as recognized by the person skilled in the art.

Examples of IOLs, illustrating various haptic configurations include those described in U.S. Pat. Nos. Des. 395,512; 5,405,386; 5,376,115; 5,306,297; 5,282,855; 5,266,241; 5,047,051; 4,863,539; 4,863,465; 4,842,600; 4,617,023; 4,502,163; 4,468,820; U.S. Des. Pat. Nos. 267,197; and 267,041 hereby incorporated by reference. Several manufactures make a posterior chamber implant (PCIOL) with a single completely enclosed eyelet on each haptic. It is believed, Allergan, Inc., offered an implant with two completely enclosed eyelets on each end of a haptic, which required passage of a suture through the eyelets. The applicant has presented a paper entitled "A Closed-Chamber, Scleral Tunnel Approach to Sutured PCIOLs," April, 1998 (San Diego, Calif.), in which the applicant disclosed a single partially enclosed eyelet on each of two haptics.

SUMMARY OF THE INVENTION

The device and method of the present invention provides an improved approach to the implantation of PCIOLs in an eye. The device and method advantageously employ a plurality of fixation eyelets, and preferably 3 or more, collectively on the haptics of the IOL. Though other sequences are possible, in one preferred procedure, sutures or other securing structure are passed into an eye and properly located. Thereafter the IOL is positioned at its ultimate site, securing the haptics to the eye with the sutures. In another particularly preferred procedure, the fixation eyelets permit mechanical securing of the IOL to the eye in situ after the sutures or other securing structure has been placed in the eye.

The device and method of the present invention offer any of a number of advantages over prior devices and methods. For instance, multi-point fixation helps to stabilize the optic and secure it from undesired movement in response to external forces. The need to guide and pass a suture through the eyelet during surgery also is obviated. Other advantages are also possible.

DESCRIPTION OF THE DRAWINGS

Further advantages of the present invention will be apparent to the skilled artisan upon review of the following detailed description, taken in connection with the accompanying drawings in which.

DETAILED DESCRIPTION OF THE PREFERRED EMBODIMENTS

Figure 1:
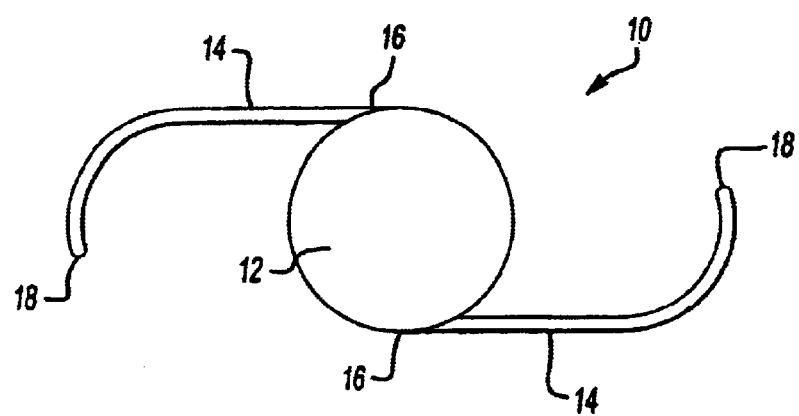
FIG. 1 is an elevation view of a conventional intraocular lens (IOL) having a haptic.

FIG. 1 illustrates one embodiment of the present invention, wherein an IOL 10 has an optic 12 and at least one haptic 14 attached to the optic (e.g., mechanically, adhesively, welded, unitarily connected or the like). Though two haptics 14 are shown, the skilled artisan will appreciate that a suitable single haptic (preferably capable of at least three-point fixation) may be employed in its place, as may three or more haptics.

Figure 2:
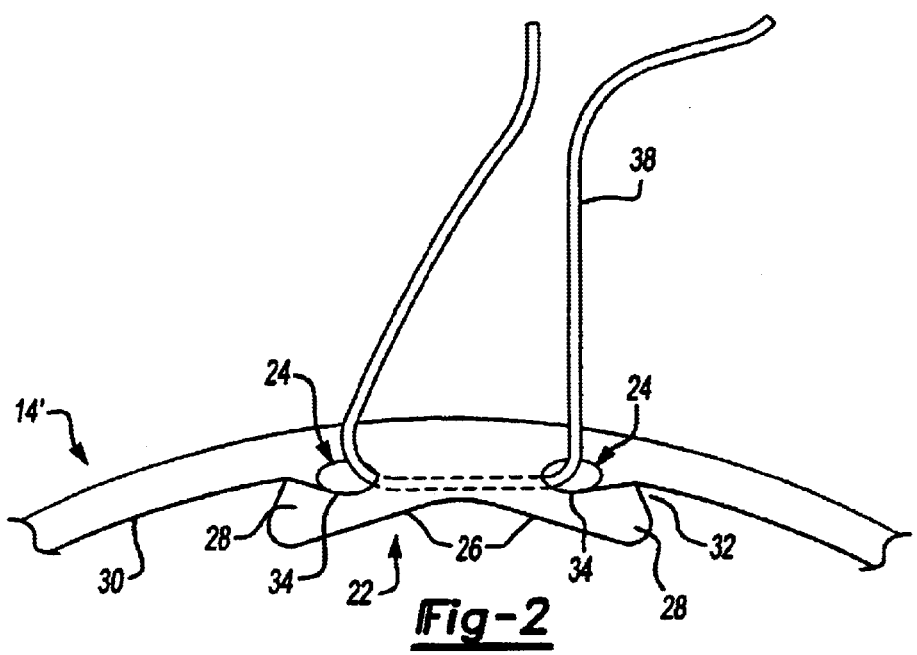
FIG. 2 is an enlarged elevational view of a section of a haptic in accordance with the present invention.

The haptics shown in FIG. 1 are connected to the optic at a first end 16 of each haptic, extending outwardly from the optic, and having a second end 18 (shown in this embodiment as a free end, though alternate structures may be employed). Referring to FIG. 2, there is shown a portion of a haptic 14' in accordance with the present invention. The haptic has an attachment structure 22 having at least one attachment eyelet 24. The number of attachment eyelets on each haptic may vary as desired. As shown in FIG. 2, two eyelets 24 are provided, though it is possible to combine multiple eyelets into a single eyelet.

Though other structures may be employed, generally the structure 22 is defined so that an aperture is provided in the haptic, access to which is provided by a notch, slit, passageway or other path so that the haptic may be snapped or hooked onto a securing member.

Thus, as FIG. 2 illustrates, each haptic includes two eyelets 24. Though shown radially inward of the haptic, the eyelets can be located radially outward of the haptic. Each eyelet is defined by an arm 26 that extends inwardly of the haptic and folds back upon itself so that its free end 28 is substantially abuttingly adjoined to an inner wall 30 of the haptic, but is maintained separable from the inner wall 30. Preferably, the free end 28 and inner wall 30 are separated at the time of manufacture, though it is possible for a surgeon or another to cut an opening subsequent to manufacture (e.g., at or near time of surgery). Though optional, FIG. 2 illustrates a structure where the inner wall 30 and the opposing end 28 of the arm 26 have an enlarged or bulbous section thickness.

A notch 32 is defined, allowing a pathway to help guide a suture or other securing member into the aperture 34 defined in the eyelet. As seen in FIG. 2, though the free end 28 is shown in proximate (or even contacting) relation to the inner wall 30, it will be appreciated that larger spacings are possible.

Though the overall attachment structure 22 is illustrated as a unitary structure relative to the haptic, it will be appreciated that separate components may be connected together to achieve a like result.

Figure 3:
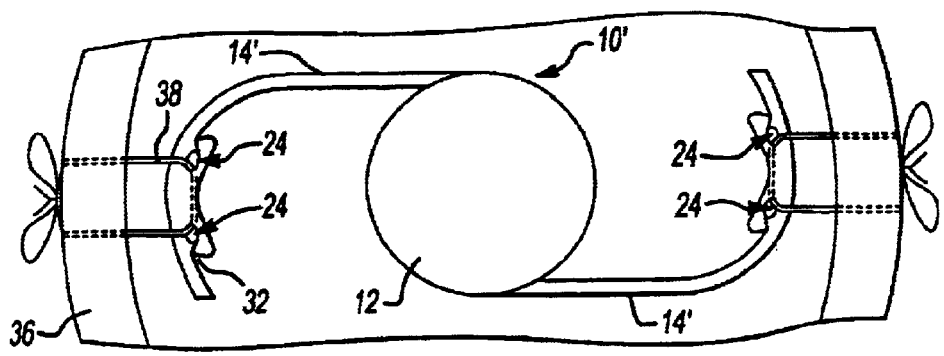
FIG. 3 is a view of an IOL in accordance with the present invention, showing the IOL being secured to an eye.

Preferably, as shown in FIG. 3, at least three eyelets 24 (at least one of which has a free end separated from the inner wall of the haptic) are provided in spaced relationship to the optic 12'. The eyelets may each be the same size or shape or they may be a different size or shape relative to the other. Moreover, multiple eyelets can be combined into a single eyelet.

In one preferred embodiment, the eyelets are spaced and positioned so that the center of the optic falls, when fixed in an eye (such as depicted in FIG. 3), within the space defined by the contact point between the eyelets and the members used to secure the haptic in the eye. Other variations may be made, nonetheless, to suitably employ a structure in which the center of the optic would fall outside such space.

Referring to FIG. 3, in a highly preferred IOL 10', four eyelets 24 are located on two haptics 14' and spaced about the optic 12', on either side of the longitudinal and transverse axes of the IOL 10', affording four attachment sites on the haptics that secure the IOL in place and resist twisting, folding or other undesired movement within the eye.

The skilled artisan will appreciate that any of a number of different haptic structures may employ eyelets in accordance with the present invention, thus, the invention is not limited to only two-haptic IOLs.

Preferably the lens portion or optic is made from one or more materials that are biocompatible and optically transparent. More preferably, such material is a synthetic or polymeric material. It may be hydrophilic or hydrophobic. The lens may be rigid or flexible, hard or soft. Though preferably, the material is a soft and flexible material. The specific material employed is the subject of ongoing research in the art and the present invention contemplates that later developed materials may suitably be employed. Thus, without limitation, examples of various suitable types of materials for the lens include methacrylates (e.g., polymethyl methacrylate), olefins (e.g, polypropylene), and silicones.

The haptic, in turn, may be the same material as the lens optic. Alternatively, other suitable materials may be employed, such as plastics (e.g., polyamides) or certain (metal) or ceramic wires or fibers. In general, the haptic material or structure is selected so that the haptic may be semi-rigid or rigid and resilient. Moreover, it should be compatible with the lens optic sufficient so that it may be anchored or staked to the optic (if not formed integral with the optic). The present devices and procedures are illustrated by reference to a posterior chamber IOL (PCIOL). It should be appreciated, however, that the haptic structures of the present invention may be incorporated into other devices implanted into the human body, including but not limited to, intraocular implants with or without an optic, such as iris implants (for instance, for replacing the iris) or endocapsular tension rings, modified endocapsular tension rings, segments, arcs, arms, or other members.

In accordance with the process of the present invention, the IOL is secured in the eye by insertion in the posterior chamber, such as following cataract surgery or replacement of a preexisting IOL. The haptics are secured to structure within the eye by a securing member such as a suture 38 (as shown in FIGS. 2 and 3) through the apertures 34 of the eyelets 24 so that the suture resides in mating, nesting or other suitable relationship with the eyelets associated with the haptic.

Either before or after insertion of the IOL into the posterior chamber, a suitable amount (if any) of a generally viscoelastic material or other suitable material may be filled in the anterior and posterior chamber to occupy the volume left empty by removal of, for instance, a cataract and the anterior chamber aqueous fluid.

An IOL in accordance with the present invention is inserted through an incision into the anterior or posterior chamber. The IOL may be folded or compressed as desired to facilitate insertion. In one preferred embodiment of the present invention, the site where the IOL is to reside in the eye is prepared to include at least one, and preferably 3 or more securing members. The securing members can be hooks, stakes or some other arm or member. Preferably the securing members are at least a portion of a suture that has been located and placed in the eye before or when the IOL is inserted. The present invention also contemplates passing a suture after the IOL has been inserted.

With or without the aid of the associated notches 32, the apertures of the eyelets associated with the haptic are aligned with the securing members and the haptics are then secured to the securing members, such as by snapping the securing members through the space defined between the inner wall 30 of the haptic and the free end 28 of the arm 26.

In a highly preferred embodiment, two securing members are formed with a suture 38 (which may be loose to afford extra slack or length for attachment), preferably a double armed suture, the ends of which are passed through the sclera 36, spaced a suitable distance apart (e.g., about 1 to about 2.5 mm and more preferably about 1.75 mm), such as by a paracentesis in a closed system. The suture loop is easily retrieved and snapped onto the haptic through each port. The haptics may then be guided with the suture into the ciliary sulcus and the implant secured.

In addition to the ability to navigate the haptics and IOL into place by use of the suture, the sutures also permit the surgeon to apply tension and unfold or otherwise maneuver the IOL into proper place. Suitable knotting can also be done whereby suture knots are not exposed, owing to an external knot, either with or without a scleral flap. The structure of the present haptic also enables the rotation of externally tied suture knots internally or inwardly to reduce the likelihood of wear or abrasion. As shown in FIG. 3, the present invention permits both arms of a suture loop to pass on the same side of the haptic, with either or both below or above the haptic. As FIG. 3 further illustrates, for a two haptic implant, the implant provides four points of fixation. In combination with the four points of fixation through the sclera, a total of eight fixation points are provided per eye.

Referring to FIGS. 4–8, in one embodiment, particularly when an IOL having the haptic structure of FIGS. 2 and 3 is employed, to aid the surgeon in passing a suture into the eye and positioning it in registered alignment with the apertures of the eyelets of the haptic, a guide device 40 is employed. The guide device 40 preferably has a base portion 42, referred to also herein more specifically as a gripping portion 42 (which may be gripped by a surgeon or by another instrument) with at least two guide channels 44 defined therein into which a suture 46 and needle 48 may be placed. As shown in FIG. 3, preferably the longitudinal axis of each guide channel is substantially parallel to one another, although other non-parallel paths may be employed, provided that the terminal ends 50 of the channels of the guide device are spaced approximately the same distance of the spacing between the eyelets of the haptic. For instance, where the eyelets are about 1.75 mm apart, so are the ends of the channels.

Figure 4:
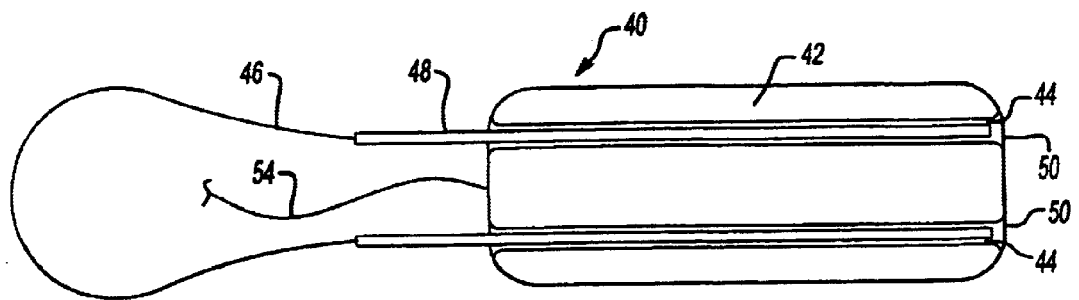
FIG. 4 is a sectional view of suture guide in accordance with the present invention.
Figure 5:
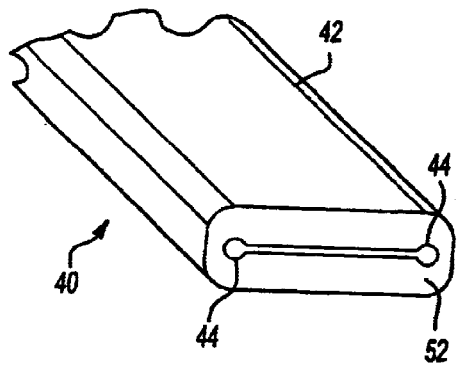
FIG. 5 is a perspective view of a suture guide, in accordance with the present invention.
Figure 6:
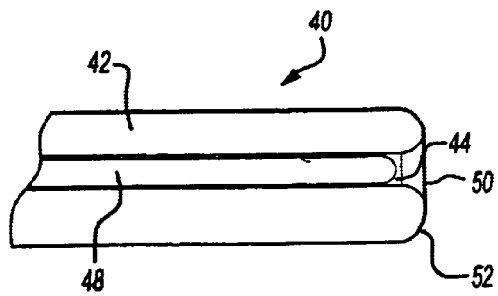
FIG. 6 is a side sectional view of the drawing of FIG. 5 taken along a longitudinal axis of a bore in the drawing of FIG. 5.
Figure 7:
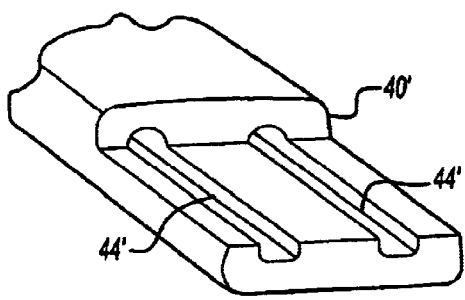
FIG. 7 is a perspective view of another suture guide body section in accordance with the present invention.
Figure 8:
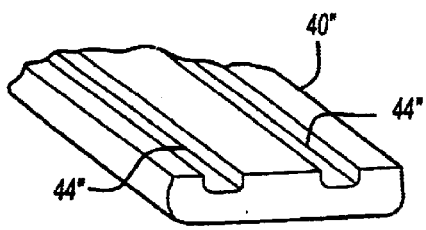
FIG. 8 is a perspective view of yet another suture guide body section in accordance with the present invention.

In one highly preferred embodiment, the device has a gripping portion having two channels. The gripping portion terminates at an end that has a blunted periphery portion or tip 52 that surrounds the terminal ends of the guide channel. The periphery portion is shown as rounded in the embodiment of FIGS. 4–6, however, any other configuration may be employed, provided that the tip has substantially no sharp edge that could snag or otherwise induce trauma to the eye when the suture is passed. Optionally a soft material may be used at the tip. Preferably, prior to when the suture is passed, but when the suture is placed into the eye at the outset, the free end of the suture and needle is recessed or otherwise spaced from the tip 52, as FIGS. 4 and 6 illustrate.

Preferably the channels defined in the of the guide device are substantially smooth and provides little frictional resistance. Any suitable material may be employed. The suture guide device 40 may be used manually or in conjunction with another instrument for helping to feed or otherwise advance a suture through the channels. Moreover, the guide device may be incorporated into an ergonomically comfortable hand piece for the surgeon. The embodiment of FIG. 4 optionally includes a retrieval member 54, such as a flexible cord, a finger or the like to assist the surgeon in extracting the guide device from the eye.

The channels may be bores, i.e., substantially defined about its entire periphery by a wall of the base or gripper portion along the entire length. Alternatively, they may be enclosed over by the wall over only a portion of the length, such as illustrated in the device 40' (having channels 44') in FIG. 8. They may also be an open channel structure, such as depicted in the device 40" (having channels 44") of FIG. 8. Moreover, though shown as a solid body, the body or gripping portion may include spaced apart guide channels that are devoid of some or all of the structure between them over at least a portion of the length.

While the present guide device is particularly attractive for use in procedures employing a haptic structure such as in FIGS. 2–3, it may be used in any procedure, particularly those in which two or more sutures are to be passed substantially simultaneously.

As to the foregoing detailed description, the discussion of procedures performed by a surgeon is not intended as limited to certified ophthalmologic surgeons. Rather it is intended more broadly, and includes any health care provider.

The devices of the present invention may be provided individually or together as a kit, either with or without other surgical instruments or supplies including but not limited to scalpels, trays, forceps, needles, sutures, antiseptics, swabbing, or a combination thereof. Moreover, the devices may be included in a system that includes surgical equipment such as phacoemulsification apparatus, irrigation devices, or the like.

EXAMPLE I

The skilled artisan will recognize that any of a number of different suture techniques may be employed. The present example illustrates but one and is not intended as limited.

A scleral tunnel incision is created on the steep axis, usually temporally, then a paracentesis is created about 2 clock hours to the right of the incision. A trapezoidal configuration of the paracentesis allows easier positioning for the passage of the trans-scleral fixation sutures to either direction. The anterior capsule is filled with a viscoelastic material in connection with this step.

A double armed 10-0 Prolene suture is passed through the ciliary sulcus. The two suture ends are passed through the sclera about 1.75 mm apart and about the three hours counterclockwise. A second double armed suture is passed in a similar fashion for the site 180 degrees away.

The suture loops are retrieved from the scleral site with a Kuglen hook. They can both be retrieved at this stage, or retrieval of the proximal loop can wait maintaining the proximal suture loop at the paracentesis site of storage until ready to attach that loop to the trailing haptic.

The IOL is brought to the operative site and is attached to the leading haptic to the distal suture loop. This is done by holding the haptic with a forceps on the optic side of the eyelet and slipping the loop of suture into the eyelet via its notch. During this step, the IOL still has not had any contact with the ocular surface.

The leading haptic of the IOL is then guided into the distal ciliary sulcus and the suture is tied externally and snugged into position. The process is repeated for the proximal suture loop and the trailing haptic, achieving a well positioned implant, having four point fixation associated with each side of the implant (two points on each haptic and two points on the sclera). The knots are rotated internally. Optionally, viscoelastic is placed on the knot to facilitate rotation.

The resulting implants are substantially free of lens tilt and decentration. It will be appreciated that other procedures may be combined with the present, such as astigmatic limbal relaxing incisions. Moreover, the procedure can be employed for sutured PCIOL in aphakia, IOL lens exchange, or in a setting of traumatic cataract, or in the setting of iris implants.

Accordingly, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims. All patents and other publications cited herein are expressly incorporated by reference.

What is claimed is:

1. A haptic for an ophthalmological implant comprising:

a) an arcuate haptic having an inner wall;

b) at least two spaced apart eyelets on said haptic adapted for receiving a securing member, and attaching onto said securing member, wherein at least one of said eyelets is defined by a free end of an arm that is substantially abuttingly adjoined to said inner wall of said haptic and is adapted to be separated from said inner wall of said haptic, wherein each of said eyelets includes an aperture defined by an arm that depends from said haptic and folds over upon itself, and wherein a notch is defined at said arm for guiding a securing member into said eyelet.

2. The haptic of claim 1 further comprising an optic secured to said haptic.

3. The haptic of claim 2 further comprising a second haptic having two spaced apart eyelets.

4. The haptic of claim 3 wherein the eyelets are spaced and positioned so that the center of said optic falls, when fixed in an eye, within the space defined by a contact point between the eyelets and said securing member.

5. The haptic of claim 3, wherein the haptic provides four attachment sites for securing in an eye.

6. The haptic of claim 2 wherein said eyelets depend inwardly toward said optic relative to said haptic.

7. The haptic of claim 2 wherein the eyelets are spaced and positioned so that the center of said optic falls, when fixed in an eye, within the space defined by a contact point between the eyelets and said securing member.

8. A method for implanting a haptic into an eye comprising the steps of:

a) providing an implant having at least one arcuate haptic defining an inner wall, said haptic including at least two spaced apart eyelets adapted for receiving a securing member and attaching onto said securing member, wherein at least one of said eyelets is defined by a free end of an arm that is substantially abuttingly adjoined to said inner wall of said haptic and is adapted to be separated from said inner wall of said haptic, wherein each of said eyelets includes an aperture defined by an arm that depends from said haptic and folds over upon itself, and wherein a notch is defined at said arm for guiding a securing member into said eyelet;

b) inserting a securing member into an eye; and c) attaching said haptic to said securing member.

9. A method according to claim 8 wherein said implant is an intraocular lens.

10. A method according to claim 8 wherein said securing member is a suture.

11. A method according to claim 10 wherein said inserting step employs a suture guide device having at least two channels defined therein for guiding a suture through each channel and into an eye.

12. A method according to claim 10 wherein said suture is passed through a sclera of an eye.

13. A method according to claim 12 wherein upon said attaching step the haptic is secured to the eye by four point fixation.

14. A method according to claim 8 further comprising a second haptic that is secured to the eye by a suture.

* * * * *